United States Patent
Moore et al.

(10) Patent No.: US 7,701,576 B2
(45) Date of Patent: Apr. 20, 2010

(54) METHOD FOR SORTING AND ANALYZING PARTICLES IN AN AEROSOL WITH REDUNDANT PARTICLE ANALYSIS

(75) Inventors: Robert R. Moore, Vancouver, WA (US); Mary V. Moore, Vancouver, WA (US); Joseph G. Birmingham, Vancouver, WA (US)

(73) Assignee: MicroStructure Technologies Inc., Vancouver, WA (US)

( * ) Notice: Subject to any disclaimer, the term of this patent is extended or adjusted under 35 U.S.C. 154(b) by 328 days.

(21) Appl. No.: 11/764,164

(22) Filed: Jun. 15, 2007

(65) Prior Publication Data

US 2008/0309919 A1    Dec. 18, 2008

(51) Int. Cl.
*G01N 21/00*     (2006.01)

(52) U.S. Cl. ...................................... 356/338

(58) Field of Classification Search ............. 356/72, 356/73, 338; 250/306, 288
See application file for complete search history.

(56) References Cited

U.S. PATENT DOCUMENTS

| | | | | |
|---|---|---|---|---|
| 4,765,737 A | * | 8/1988 | Harris et al. | 356/336 |
| 5,180,065 A | * | 1/1993 | Touge et al. | 209/577 |
| 5,578,460 A | * | 11/1996 | Ebersole et al. | 435/29 |
| 5,989,824 A | | 11/1999 | Birmingham et al. | |
| 6,010,554 A | | 1/2000 | Birmingham et al. | |
| 6,110,247 A | | 8/2000 | Birmingham et al. | |
| 6,400,453 B1 | * | 6/2002 | Hansen | 356/237.1 |
| 6,657,713 B2 | * | 12/2003 | Hansen | 356/237.1 |
| 7,178,380 B2 | | 2/2007 | Shekarriz et al. | |
| 7,355,696 B2 | * | 4/2008 | Mueth et al. | 356/244 |
| 2002/0179499 A1 | | 12/2002 | Kenning et al. | |
| 2004/0008345 A1 | | 1/2004 | Nurmikko et al. | |
| 2005/0105079 A1 | * | 5/2005 | Pletcher et al. | 356/72 |
| 2005/0189484 A1 | * | 9/2005 | Glukhoy | 250/287 |
| 2006/0093737 A1 | | 5/2006 | Dick et al. | |
| 2006/0252095 A1 | | 11/2006 | Hill et al. | |
| 2007/0195310 A1 | * | 8/2007 | Kanda | 356/73 |

* cited by examiner

*Primary Examiner*—Tarifur R. Chowdhury
*Assistant Examiner*—Isiaka O Akanbi
(74) *Attorney, Agent, or Firm*—Bacon & Thomas, PLLC

(57) ABSTRACT

A method and apparatus for sorting and performing redundant analysis of particles in an aerosol is disclosed. Redundant analysis reduces the possibility of false positive analyses, which is advantageous in the art. The apparatus may comprise an aerosol concentrator, an optical particle analyzer, an electrosprayer and a charged particle analyzer. A method according to the invention may comprise delivering a concentrated aerosol stream to an optical particle analyzer; analyzing each particle of interest and selectively triggering an electrosprayer to electrospray each particle of interest; adding a charge to the particle, which is then moved by electrostatic forces to a charged particle analyzer; and performing a second, redundant analysis of each charged particle collected on the charged particle analyzer to confirm the identity of the particle of interest. The apparatus and method may also be adapted to perform redundant analysis of disguised particles that are coated to disguise their payload.

10 Claims, 7 Drawing Sheets

Aerosol (100)

↓

First Concentrator (200)

↓ ↘

Additional Concentrator (250)

↓ ↙

First Optical Analyzer (300)

↓

First Electrosprayer (400)

↓

First Charged Particle Analyzer (500)

↓

Bio-Analysis (e.g., PCR) (600)

FIG. 1a

Aerosol (100)

```
┌─────────────────────────────┐
│   First Concentrator (200)  │
└─────────────────────────────┘
         │            │
         │            ▼
         │   ┌──────────────────┐
         │   │    Additional    │
         │   │ Concentrator (250)│
         │   └──────────────────┘
         ▼            │
┌─────────────────────────────┐
│  First Optical Analyzer (300)│
└─────────────────────────────┘
              │
              ▼
┌─────────────────────────────┐
│   First Electrosprayer (400) │
└─────────────────────────────┘
              │
              ▼
┌─────────────────────────────────────┐
│  First Charged Particle Analyzer (500)│
└─────────────────────────────────────┘
              │
              ▼
┌─────────────────────────────────────────────┐
│ Breach Coating of particle (e.g., via Plasma Lysis) (650) │
└─────────────────────────────────────────────┘
                           │
                           ▼
              ┌─────────────────────────────┐
              │  Second Concentrator (700)  │
              └─────────────────────────────┘
                           │
                           ▼
              ┌─────────────────────────────┐
              │ Second Optical Analyzer (800)│
              └─────────────────────────────┘
                           │
                           ▼
              ┌─────────────────────────────┐
              │ Second Electrosprayer (900)  │
              └─────────────────────────────┘
                           │
                           ▼
              ┌─────────────────────────────────┐
              │ Second Charged Particle Analyzer (1000)│
              └─────────────────────────────────┘
```

FIG. 1b

METHOD FOR SORTING AND ANALYZING PARTICLES IN AN AEROSOL WITH REDUNDANT PARTICLE ANALYSIS

FIELD OF THE INVENTION

The field of the invention is methods and apparatus for sorting and analyzing particles in an aerosol. An aerosol is generally defined as any gaseous fluid containing particles. For purposes of the present invention, most samples of ambient air are aerosols. A prompt analysis of particles in an aerosol has many applications. Terrorists and bombers may seek to plant explosive devices so as to cause destruction, injury and death. If such terrorist or bomber has particles of the explosive on his or her person, then an analysis of the particles in the air surrounding the person may allow for the early detection of a terrorist or bomber. If the terrorist seeks to cause injury of a targeted group by exposure to a chemical agent such as nerve gas, a pathogen such as a virus or bacteria, or a radioactive composition, then prompt detection of the attack may allow defensive measures to be taken, so as to minimize the injury and death.

BACKGROUND OF THE INVENTION

This invention pertains to the field of collecting, sorting and analyzing particles in an aerosol and, more particularly, to a method and apparatus for collecting an aerosol, sorting particles within the aerosol and subjecting the particles to redundant analysis for the purpose of identifying the particles.

The separation and capture of particles or aerosols from air or other fluid streams are of concern in two contexts: first, in determining the type and concentration of such particles/aerosols and, second, in cleansing the fluid stream for subsequent use. For example, the detection or extraction of airborne biological or chemical warfare agents, biological contamination in confined spaces, such as aircraft or hospitals, or industrial pollutants (either in ambient air or in smokestacks) may be required in various scenarios.

Much effort has been expended in the past in the collection of aerosols, the extraction of particles from aerosols and the analysis and identification of particles in aerosols.

The prior art includes methods and apparatus for analyzing particles in gases in possible target areas, including public buildings, critical infrastructure such as water supply facilities, and defensive installations such as military bases. The prior art includes sampling of the atmosphere from possible target areas. In some prior art technologies, all of the particles from a sample are isolated, and then the particles are analyzed. In other prior art methods, the volume of the sample is reduced, and a representative portion of the particles is analyzed.

The prior art recognizes that the avoidance of false positives is of critical importance. A false positive with respect to explosive particles, pathogen particles, radioactive particles, and any other adverse particles, may lead to unnecessary evacuations and possible injury and death. In addition, if a particular method and apparatus result in repeated false positives, then the level of confidence in that method and apparatus may be degraded to the point that vigorous responses to protect the public will become difficult to achieve. However, to date, none of the prior art adequately addresses the problem of false positives.

SUMMARY OF THE INVENTION

A method and apparatus for sorting and analyzing particles in an aerosol with redundant particle analysis is achieved by the present invention. This redundant particle analysis reduces false positives.

In one embodiment of the invention, a stream of an aerosol enters the first concentrator of the apparatus. The first concentrator removes the majority of the gas from the aerosol to provide a first concentrated aerosol that is fed to a first optical analyzer. In another embodiment of the invention, a stream of an aerosol passes through multiple concentrators to provide a first concentrated aerosol.

The stream of the first concentrated aerosol passes through the first optical analyzer of the apparatus, which exposes the particles in the first concentrated aerosol to one or more lasers. The lasers may comprise infrared lasers, ultraviolet lasers, and combinations thereof as well as other lasers. The first optical analyzer analyzes the scattering and/or absorption of one or more of the laser beams that is caused by the particles, and recognizes any particles of interest based on scattering and/or absorption characteristics.

The first concentrated aerosol flows from the first optical analyzer to the first electrosprayer, which comprises a first electrospray nozzle, a supply of a first electrospray fluid, and a first electrospray trigger. In a preferred embodiment, the electrosprayer also comprises a controller and a high voltage power supply. In one embodiment of the invention, the first electrosprayer may comprise multiple electrospray fluid reservoirs, with different electrospray fluids suited for administering to different types of particles of interest. The first electrospray trigger fires the first electrospray nozzle to apply the first electrospary fluid to one or more selected particles of interest. The timing of the firing may be calculated based upon the distance between the laser scattering in the first optical analyzer and the first electrosprayer, as well as the flow rate of the first concentrated aerosol through the apparatus. The application of an electrospray fluid to a particle of interest causes the particle to become electrically charged and attracted by electrostatic forces to a first charged particle analyzer located downstream of the electrosprayer. The first charged particle analyzer is preferably a micropillar array. Micropillar arrays are disclosed in U.S. Pat. No. 6,110,247.

The method and apparatus of the present invention are particularly advantageous in allowing for redundant particle analysis. A particle of interest is initially detected and analyzed by the first optical analyzer. This analysis is later confirmed when the same particle is coated with an electrospray fluid and attracted to the first charged particle analyzer, on which a second analysis of the same particle may be performed. The redundant analysis of a particle of interest by both the first optical particle detector and the first charged particle analyzer significantly reduces the possibility of a false positive and improves over the prior art.

The initial analysis by the first optical analyzer may be based upon a comparison of the scattering and/or absorption caused by the particle under interrogation to the known results of interrogation of particles of interest. Particles of interest include adverse particles such as particles of explosives, biological particles such as viruses and bacteria, and radioactive particles, each of which may be known to cause injury, disease and/or death.

In addition, the present invention is capable of dealing with particles of interest that may be disguised particles. Terrorists and the like seeking to cause disease, injury or death, may disguise adverse particles with coatings that are designed to avoid detection. For example, an adverse particle known to cause disease, injury or death, may be coated with a time-release substance so as to avoid detection of the adverse particle. The first optical analyzer may be programmed to recognize such coatings, and designate the relevant particle to be a particle of interest for further analysis, such as when the particle of interest is collected on the first charged particle analyzer.

In one embodiment of the invention, the first optical analyzer may comprise an ultraviolet laser, an infrared laser, and a source of visible electromagnetic radiation to allow interrogation of the infrared, ultraviolet and visible spectra generated by the particles in the first concentrated aerosol stream.

In another embodiment of the invention, the first optical analyzer may comprise a split beam. For example, the beam from an infrared laser may be split into a first beam and a second beam, so that the first concentrated aerosol stream passes first through the first beam, and subsequently through the second beam. The distance between the first beam and the second beam may be fixed. The first optical analyzer may then compare the interrogation of particles by the first beam and the second beam. The particles in the first concentrated aerosol stream may have unique spectra (both absorption and transmission). Thus, the precise time at which a particular particle passes through the first beam may be compared to the precise time at which that particle passes through the second beam, so as to allow precise calculation of the speed of the particle as it enters the first electrosprayer. This may allow for a more precise triggering of the electrospray nozzle, and thus significantly reduces the possibility that a particle not considered to be of interest is coated with an electrospray fluid.

In one embodiment of the invention, the first charged particle analyzer may comprise multiple rows of micropillars. The diameters of the micropillars may decrease in each row. Thus, the diameter of the micro pillars in the first row may be larger than the diameter in the second row, and the diameter of the micropillars in the second row may be larger than the diameter of the pillars in the third row, and so forth. This may facilitate the collection of larger particles on the first row, particles of smaller size on the second row, particles of still smaller size on the third row, and so forth.

The particles on the micropillars may undergo a second analysis in a number of different manners. The electrospray fluid may comprise a fluorescent tag that fluoresces when it becomes attached to a particle of a particular composition. For example, there may be a source of electrospray fluid that comprises a fluorescent tag that fluoresces when it comes into contact with a particle of a particular pathogen. If this fluorescence is detected on the micropillars, then the presence of that pathogen has been detected and/or confirmed.

The particles on the micropillars may also be subjected to Raman spectroscopy. Generally speaking, Raman spectroscopy looks for a shift in the spectra caused by a particular particle and may use radiation in the ultraviolet, infrared or visible range of the electromagnetic spectrum.

The redundant particle analysis of the method and apparatus of the present invention may require an additional step of lysis when a disguised particle is detected. A disguised particle may comprise an adverse particle such as a bacterium, which may be referred to as the payload, and a coating, which may be referred to as the disguise. If a disguised particle is detected by the first optical analyzer, then the first electrosprayer may be triggered to coat the disguised particle with an electrospray fluid, which causes the disguised particle to develop an electrical charge and be attracted to the first charged particle analyzer by electrostatic forces. The payload within a disguised particle may be impossible to verify unless the disguise is removed by removing the coating of the particle.

The disguised particle may be exposed to plasma lysing, which breaches the coating on the particle and exposes the payload. The payload particle may then be further analyzed. For example, the payload particle may be introduced into a second concentrated aerosol stream, which is fed into a second optical analyzer, then into a second electrosprayer, and subsequently into a second charged particle analyzer. This may allow for the sorting and analysis of the payload particle in the same manner that particles are sorted and analyzed by the first optical analyzer, the first electrosprayer, and the first charged particle analyzer.

In another embodiment of the present invention, the payload particle may be extracted from the first charged particle analyzer into a liquid, and analyzed by polymerase chain reaction (PCR), antigen assay, and/or other biosensor techniques. Other embodiments of the invention may comprise multiple optical analyzers, multiple electrosprayers and multiple charged particle analyzers.

BRIEF DESCRIPTION OF THE DRAWINGS

FIGS. 1a and 1b are flow diagrams of different embodiments of the present invention.

DETAILED DESCRIPTION

Figure 2:
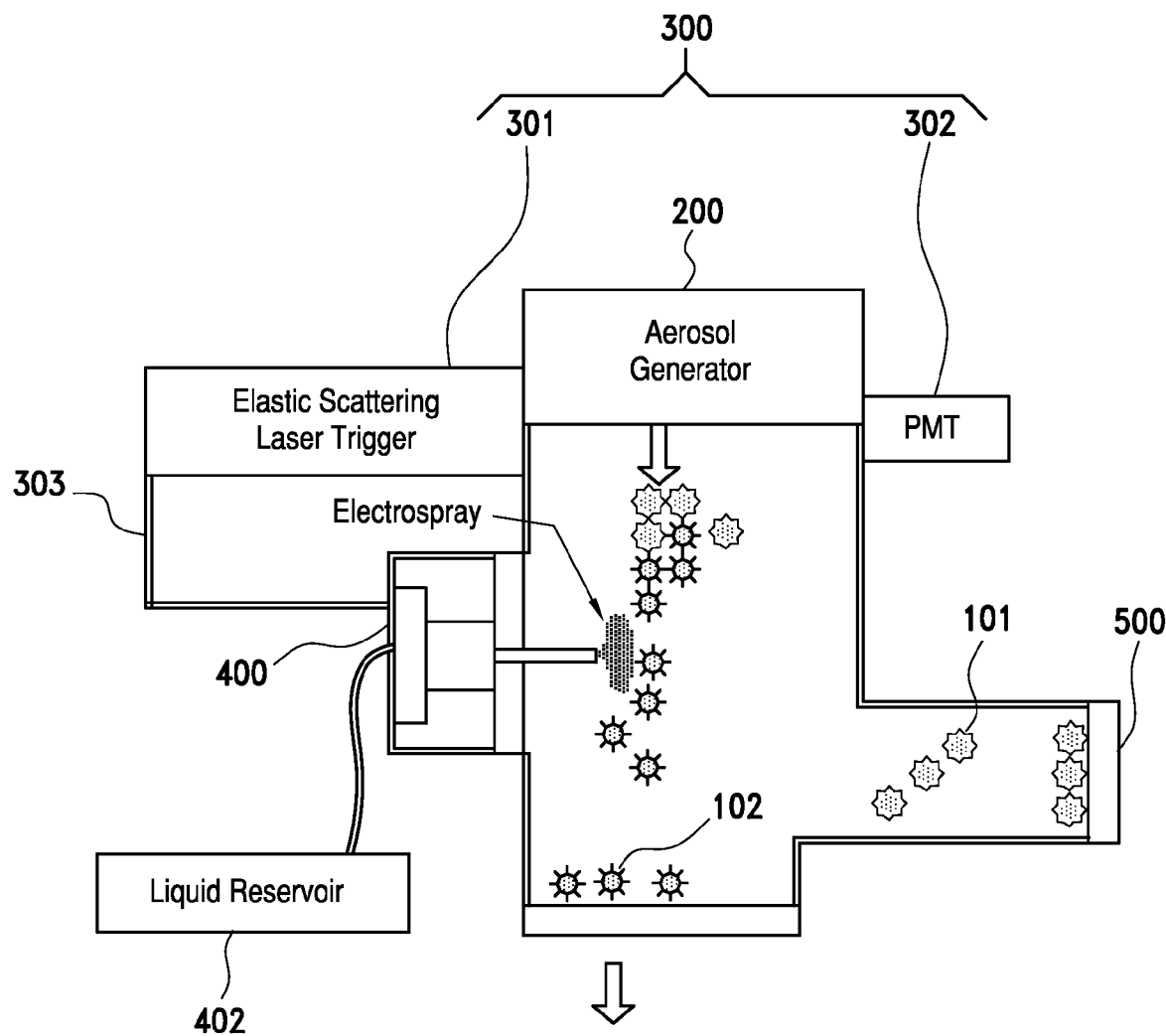
FIG. 2 is a schematic view of the present invention.

As used in this specification, the following terms shall have the following definitions unless the context indicates otherwise:

Aerosol—a suspension of particles in a fluid;

Particle—any separately identifiable solid, liquid, aerosol or other component entrained in a fluid stream that has a greater mass than the fluid forming the fluid stream, and is the subject of separation and collection for analysis;

Fluid—any fluid susceptible to fluid flow, which may comprise a combination of liquids and gases, and which may entrain foreign particles therein.

The first embodiment of the present invention comprises an apparatus for sorting and analyzing particles in an aerosol. The four main components of the apparatus generally include a concentrator, an optical particle analyzer, an electrosprayer, and a charged particle analyzer.

As shown in FIG. 1a, the first concentrator 200 collects ambient aerosol sample 100 and provides concentrated aerosol to the first optical analyzer 300, which is located downstream from the aerosol concentrator 200. An optional additional concentrator 250 may also be present between the first concentrator and first optical analyzer in order to further concentrate the aerosol 100. Particles in the concentrated aerosol passing through the optical particle analyzer 300 are then passed through the electrosprayer 400, which is located downstream from the optical particle analyzer 300. Upon passing through the electrosprayer 400, selected particles in the concentrated aerosol are sprayed with an electrospray fluid, which preferably adds a charge to the selected particles. Next, the electrosprayed particles are collected on the first charged particle analyzer 500 located downstream from the electrosprayer 400. The first charged particle analyzer 500 provides the opportunity to perform a second analysis on the charged particles collected on the first charged particle analyzer 500, thereby confirming earlier analysis performed by the first optical analyzer 300.

As also shown in FIG. 1, analysis of the particles that are collected on the first charged particle analyzer may further comprise bio-analysis 600, such a polymerase chain reaction (PCR), antigen assay or other known bio-analysis techniques. Particles that are not disguised by a coating are suitable for bio-analysis on the first charged particle analyzer.

However, in the case where the particle is disguised by, for example, a coating, the disguise is breached to expose the payload as shown in FIG. 1b. Breaching 650 the coating of the particle may be accomplished by, e.g., plasma lysis, which will penetrate the coating and expose the payload particle. The payload particle may be passed to a second concentrator 700, second optical analyzer 800, second electrosprayer 900 and second charged particle analyzer 1000. The payload particle is thus analyzed and identified in the same manner as described above with respect to a non-disguised particle. As with the first concentrator, the first optical analyzer, the first electrosprayer and the first charged particle analyzer, the present invention allows the second concentrator, second optical analyzer, second electrosprayer and second charged particle analyzer to perform redundant analysis of the payload particle.

FIG. 2 illustrates a schematic of components of the apparatus according to the present invention. The first concentrator 200 collects an ambient aerosol, concentrates the aerosol by exhausting fluid without significant loss of particles and then passes the concentrated aerosol to the first optical analyzer 300. In FIG. 2, the aerosol passed into the system from the concentrator comprises particles of two types, one being of interest and the other not. The optical particle analyzer comprises at least one laser 301 and a photomultiplier tube (PMT) or other suitable optical or electronic detector 302. The laser 301 fires one or more laser beams at the passing particles. The detector 302 then measures the scattering and/or absorption of each laser to determine the identity of each particle. Along with scattering and absorption characteristics, size and velocity of the particles as well as fluorescent signatures of the particles may also be used to identify any particle of interest.

Having conducted the first analysis of each particle, the first optical analyzer 300 sends a signal to the electrosprayer 400 via data transferring line 303, and the signal is used to instruct when and at which particles to fire the electrospray fluid. These parameters are determined primarily by, e.g., the velocity measurements of the particles measured/calculated by the first optical analyzer 300. As shown in FIG. 2, the data collected from the first optical analyzer 300 has instructed the electrosprayer to fire electrospray fluid at particles of interest 101, but not other particles 102.

Electrospray fluid is preferably stored in a reservoir 402 and supplied to the electrospray nozzle for discharging at particles. The non-electrosprayed particles 102 continue downstream in the apparatus. The electrosprayed particles 101 are electrically charged and attracted to the first charged particle analyzer 500. The other particles 102 are collected in a separate region, or may be discharged from the apparatus.

Turning now to a more detailed description of each component of an apparatus according to the present invention, the concentrator is a component of the apparatus for extracting aerosol from the surrounding environment and exhausting predominantly fluid from the aerosol. By exhausting predominantly fluid without also exhausting the particles, the concentrator produces a concentrated aerosol with only a fraction of the fluid found in the ambient aerosol. For example, the concentrator may exhaust 90% of the fluid component of the ambient aerosol, resulting in a concentrated aerosol having the same number of particles found in the ambient aerosol but with only 10% of fluid of the ambient aerosol.

The concentrator may be designed such that the fluid exhausted from the concentrator does not contain particles smaller than a predetermined size. That is to say, the concentrator may be selected such that few or no particles smaller than a specified diameter are lost in the exhaust flow and most or all particles below the specified diameter are retained in the concentrated aerosol that is passed to the optical analyzer. In this manner, the concentrator may serve as a first sorter for sorting particles in the aerosol and may be selected according to the needs of the situation.

In a preferred embodiment, the concentrator is a virtual impactor such as disclosed by U.S. Pat. No. 7,178,380. Conventional impactors comprise a nozzle above an impaction plate. In a virtual impactor, the impaction plate is replaced with a receiving nozzle that has a virtual impaction surface that is the inlet of a receiving tube. Even more preferably, the concentrator is a radial axisymmetric virtual impactor.

Figure 3:
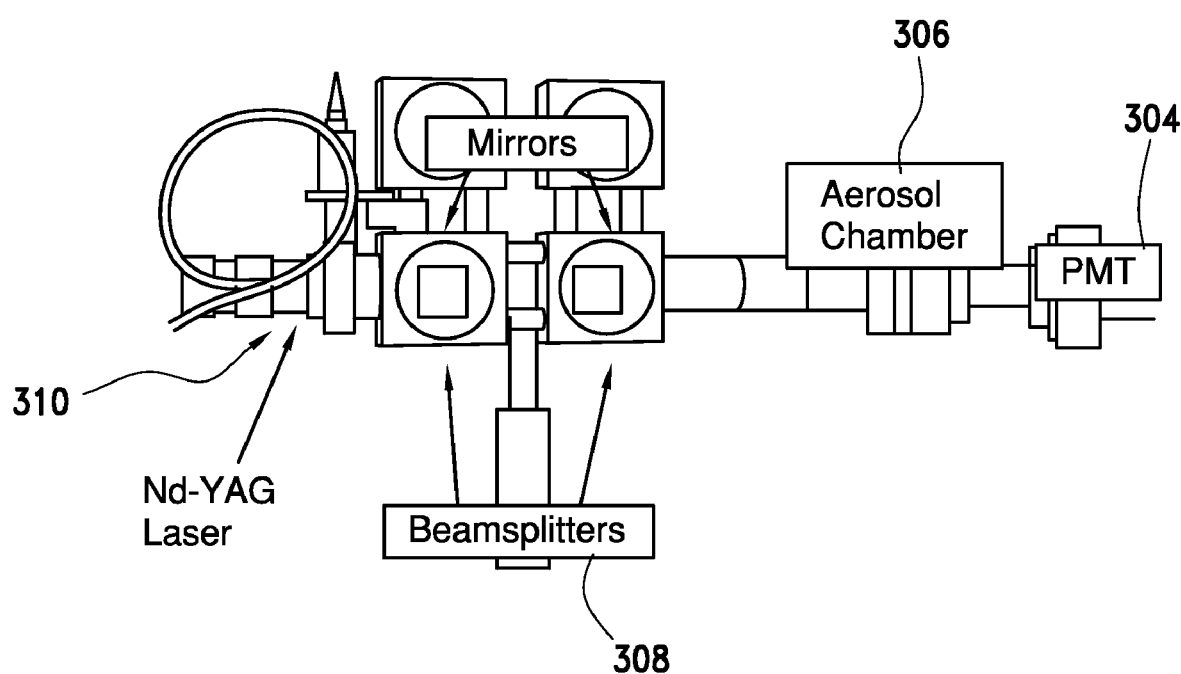
FIG. 3 illustrates an optical particle analyzer used in the present invention.

The present invention further comprises an optical analyzer, which is located downstream of the concentrator. As shown in FIG. 3, the optical analyzer 300 generally comprises a laser 310, a PMT 304 and an area 306 between the laser 310 and the PMT 304 that allows for particles to pass by and be struck by the laser beam emanating from laser 310. The laser 310 may be any laser suitable for use in elastic scattering, for example, a Nd-YAG laser, an infrared wavelength laser, or quantum cascade lasers at infrared frequencies. The laser 310 may also be protected from the aerosol by barrier flows of air, or air curtains. These air curtains prevent particles in the concentrated aerosol from contacting or damaging the laser.

In the embodiment shown, the laser 310 produces rapid pulses or a continuous beam of a single beam laser, which is split by beamsplitters 308, although the laser need not be split. The rapid pulses or continuous beam of the split beam laser collide with the passing particles, causing scattering of light. The collision of the beam with the particles may also lead to absorption of the beam by the particle. The PMT 304 measures the light scattering and/or absorption and can perform a first identification of the particles based upon these measurements.

Figure 4:
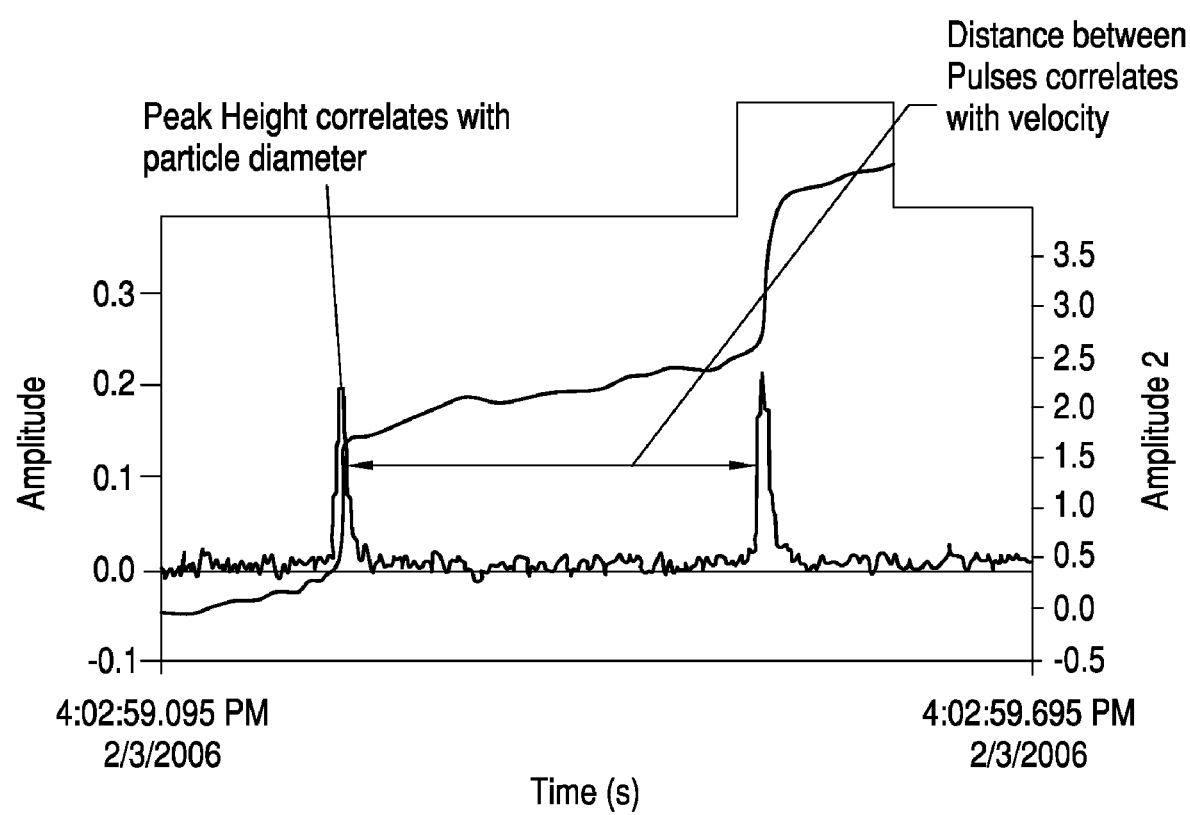
FIG. 4 is a graph showing data collected from scattering a split-beam laser with particles in an aerosol.
Figure 5:
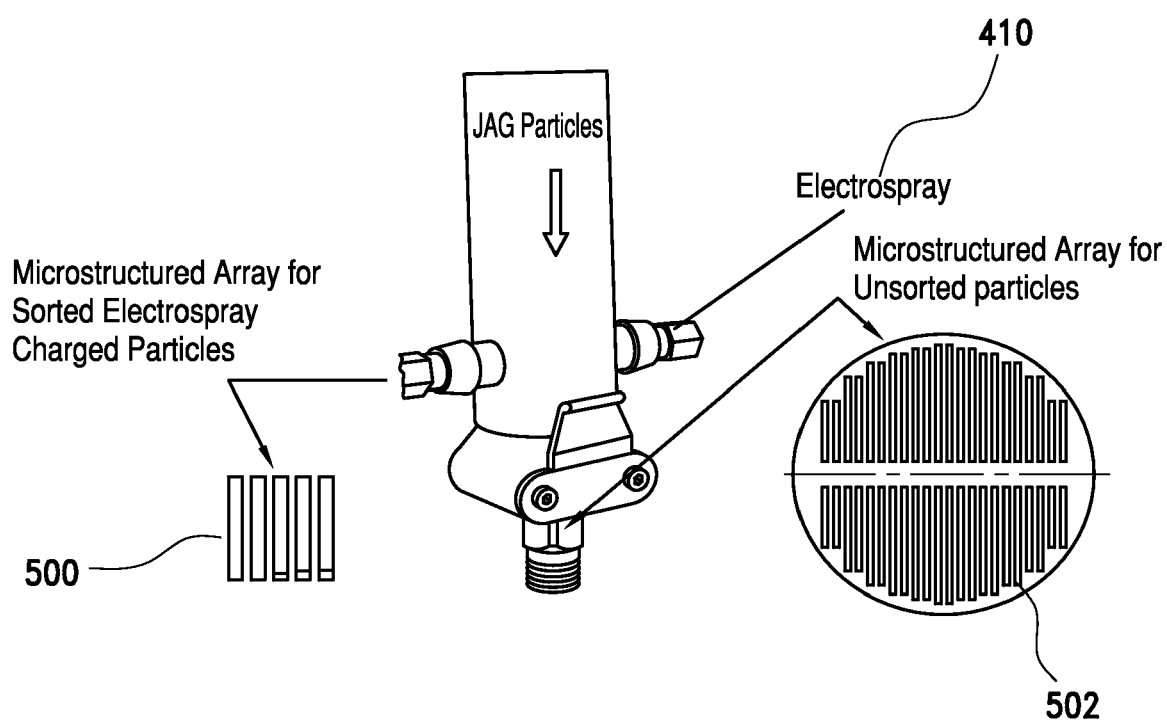
FIG. 5 illustrates an electrosprayer and a charged particle analyzer used in the present invention.

FIG. 4 shows measurements taken from light scattering in the optical analyzer, wherein the distance between pulses correlates with velocity and the peak height correlates with particle diameter. Thus, the physical characteristics of the particles may be measured in the optical analyzer.

Also, the inelastic scattering of light may be used to determine the fluorescent signatures of the particles. Certain wavelengths of light in the laser beam may interact with the particle to cause amino acids located on the particle surface, such as tryptophan, to fluoresce, thus indicating the presence of certain amino acids on the particle. The stimulated fluorescent emission may be characteristic of certain biomaterials and chemicals of interest, and therefore may be used for identification and classification purposes. The PMT 304 is capable of measuring the stimulated fluorescent emissions as well as elastic light scattering and absorption.

As alluded to above, infrared lasers that produce light that is characteristically absorbed by certain biomaterials and chemicals of interest may also be used alternative to or in combination with fluorescence to further aid in the first analysis of the particles. Again, the PMT 304 is capable of measuring whether infrared light has been absorbed.

Having now performed a first analysis of the particles as well as gathering measurements, e.g., size and velocity, of the particles, this information is used to determine when and at which particles to fire the electrospray fluid as well as what type of electrospray fluid to fire. The data from the first analysis is transmitted to the electrosprayer, where it is received and processed to select the characteristics of the spray as well as the electrospary fluid to be sprayed. Thus determined, the electrospray nozzle is triggered in order to coat the selected particle with the selected electrospray fluid.

Specifically, the velocity measurement is used to determine when to fire the electrospray nozzle based on knowing both the speed at which the particle of interest is traveling and the distance between the electrospray nozzle and the point of analysis of the particle into the optical analyzer. This distance may vary, but is preferably less than 1 cm to eliminate diverging flow.

The measurement taken to determine the size of the particle may be used to ensure that the electrospray fluid is not fired at particles which are clearly not particles of interest, such as large particles of pollen entrained in the concentrated aerosol.

Other measurements, such as the fluorescent signature measurement, are used to select at which particles to fire the electrospray fluid and also the type of electrospray fluid to be fired at the particles. For example, the fluorescence of a particle upon being subjected to the split laser beam indicates the presence of certain components on the particle which in turn may be used to identify or classify the particle. The fluorescent signature measurement may therefore be used to determine whether to fire the electrospray fluid at a specific particle and additionally the type of electrospray fluid to be fired at the particle.

Additionally, as mentioned above, a particle's absorption of infrared light may be used in a similar manner. Biomaterials and particles of interest will absorb wavelengths of infrared light and the detection of this absorption may be used to identify or classify the particles. Once identified or classified, the information is used to decide whether to fire electrospray fluid at a particle and if so, which electrospray fluid to fire at a particle.

Following the optical analyzer, the next main component of the apparatus according to a preferred embodiment of the invention, is the electrosprayer which receives the particles after they have traversed the laser beams in the optical analyzer. The electrosprayer preferably comprises a controller, a high voltage power supply, at least one electrospray nozzle and an electrospray fluid reservoir. Each electrospray nozzle is preferably comprised of at least one passage way for emitting at least one electrospray fluid.

FIG. 5 illustrates an electrosprayer 410 coupled with a first charged particle analyzer 500. The particles move downward in the direction of the arrow shown in FIG. 5 and pass through the electrosprayer. Based on the information collected and processed from the optical analyzer and discussed in more detail previously (i.e., particle velocity, particle size and particle fluorescent signature), an electrospray trigger fires an electrospary nozzle when a selected particle passes by the electrospray nozzle. The electrospray nozzle fires a short, pulsed burst of electrospray fluid to preferably coat only the specific particle passing by the electrosprayer at the time of triggering. Preferably, the initiation and termination of the burst of electrospray fluid occurs in less than one millisecond to ensure selective coating of only the particle of interest. High frequency operation of the electrosprayer enables higher particle concentration samples to be efficiently sorted and identified.

The electrospray fluid is fired at selected particles in order to add a charge to the selected particles. The electrospray fluid may also comprise an immunoassay to aid in the second identification of the particle. When the electrospray fluid attaches to the particle or particles, the particles are preferably sufficiently wetted with the electrospray fluid to prevent denaturing or dehydration resulting in drying out of the labile biomaterial or an immunoassay, if present. Similarly, if a nanoassay such as a polymer that changes the light scattering of an explosive particle is present on the particle, sufficient wetting will prevent the dehydration of the nanoassay.

Electrospray fluids comprise reagents whose fluorescence, infrared or visible and other electromagnetic radiation relates to at lease one specific binding, absorption, or reaction event. Any electrospray fluid capable of adding a charge to a particle may be used, generally speaking.

The electrosprayer may also be capable of firing multiple types of electrospray fluid in order to coat different particles with different types of electrospray fluid. In this aspect of the invention, the information collected and processed by the optical analyzer is transmitted to the electrosprayer such that the electrosprayer is instructed to fire a first electrospray at selected particles and to fire a second, different electrospray at other selected particles. In this manner, the apparatus of the first embodiment is capable of performing a second, redundant identification of multiple particles in the concentrated aerosol at once. Alternatively, the electrosprayer can be instructed to fire a first and a second electrospray at the same particle, in order to provide multiple means by which to perform redundant analysis of the particle. For example, the particle could be sprayed with both an immunoassay and an a FRET (fluorescence resonance energy transfer) probe, such that subsequent analysis and identification of the particle can be accomplished by using either of the two coatings or can be used to confirm the conclusion drawn from the first coating.

In addition, the electrosprayer may also be used to add a nanoassay to certain particles. The first analysis of the particle can also be used to initiate the addition of a nanoassay, such as antibodies with fluorescent probes, to the particle to further effect detection during subsequent particle analysis. The identification of the particle interaction with an optional nanoassay can be accomplished optically or electrically.

In another embodiment, an additional electrosprayer may be placed downstream of the concentrator and upstream of the optical analyzer. The purpose of the additional electrosprayer is to pretreat the particles in the concentrated aerosol with a fluid capable of selectively interacting with particles to produce a signature such as fluorescence.

Downstream of the first electrosprayer, the particles are sorted by a first charged particle analyzer 500 as show in FIG. 5. As shown in the FIG. 5, the first charged particle analyzer 500 is preferably located perpendicular to the general direction the particles are traveling as shown by the arrow in FIG. 5. In this configuration, the electrospray-charged particles must turn 90 degrees from the general direction of travel in order to be collected by the charged particle analyzer 500, which is preferably grounded. This movement of the particles is achieved due to the electrostatic attraction between the charged particle analyzer 500 and the electrospray-charged particles. The non-electrosprayed particles not having a charge continue in the direction of the arrow shown in FIG. 5 and preferably collect on a particle collector for uncharged particles 502.

The first charged particle analyzer, as well as the particle collector for uncharged particles may each be any size suitable for use in the apparatus of the present invention, but the first charged particle analyzer normally has an area smaller than the area of the particle collector for uncharged particles. For example, the first charged particle analyzer may have an area of about 1.96 mm$^2$, while the particle collector for uncharged particles may have an area of 19.9 mm$^2$.

In one aspect of the first embodiment, the first charged particle analyzer is a micropillar array. Micropillar arrays are disclosed by U.S. Pat. No. 6,110,247. The micropillars may be cleaned in between uses by using an ionized gas.

With the selected particles now sorted and collected on the first charged particle analyzer, the selected particles may be subjected to redundant analysis for the purpose of identifying and/or confirming the selected particles. In a preferred embodiment, any suitable means of bio-analysis, such as PCR, antigen assay, and/or other biosensor techniques may be used.

If a particle of interest is disguised, i.e., comprises a coating that prevents analysis of the payload, then the apparatus of the invention may perform plasma lysing of the coating on the disguised particle to expose the payload. The plasma lysing breaches the coating of the particle and exposes any interstitial contents for analysis. As an example, a bacterial spore can be lysed by an ionized gas to release the chromosomal nucleic acid and core proteins. Plasma lysis of particles is disclosed by U.S. Pat. No. 5,989,824.

The present invention provides for redundant analysis of the payload of disguised particles, and may include a second concentrator, second optical analyzer, second electrosprayer and second charged particle analyzer as shown in FIG. 1b and discussed above. Furthermore, duplicate samples may be processed and preserved for polymerase chain reaction replication and identification to complement the results obtained from optical analysis.

Figure 6:
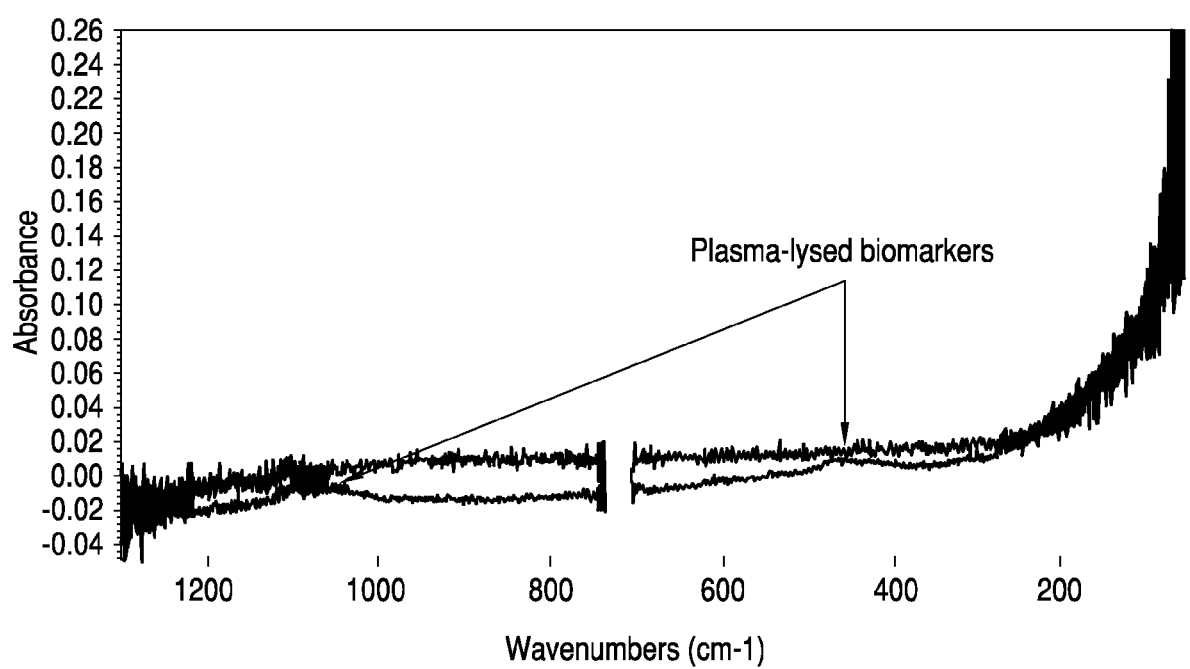
FIG. 6 is an IR spectroscopy graph comparing the data collected from a control spore group to data collected from spores of Bacillus globigii.

An example of using optical analysis for the purpose of identifying the particles is shown in FIG. 6. Plasma lysed and untreated *Bacillus globigii* (BG) spores show different spectra for 10,000 spores. The plasma lysed spectra shows peaks at 475 cm-1 and 1100 cm-1, while the control spore group does not have peaks in these areas. The 1100 cm-1 peak is believed to be the inner carbohydrate layers exposed by the ionized gas lysis which peels away the spore coat. The outer spore coats are comprised of proteinaceous materials. The source of the 475 cm-1 peak is unknown, but the peak was also shown by previous National Institute of Standards and Technology (NIST) spectra. In summary, the IR spectrum for BG spores is unique and by virtue of their carbohydrate content show strong absorption around 1100 cm-1. BG spores have these biomarkers but other biological material and interferents do not. Therefore, plasma lysis coupled with IR spectroscopy should provide a rapid, definitive detection approach.

The apparatus of the first embodiment allows for redundant confirmation of single particles, which reduces or eliminates false positives. The levels of redundant confirmation may include:

First Detection—Sample interrogation via the optical particle analyzer of the particle characterizes the particle by size and threat potential (i.e. surface composition).

Second Detection—Electrosprayed immunoassays that attach to target-binding sites of particles facilitate optical detection of nucleic acids or other molecular targets such as proteins.

Third Detection—IR spectroscopic interrogation of the charged particle analyzer is enhanced by sample enrichment and the reduction in background clutter.

Fourth Detection—Plasma lysis (i.e. ionized gas treatment) of the particles further enhances spectroscopic interrogation as well as extraction of nucleic acids and proteins for subsequent identification, and is especially useful when dealing with disguised particles.

Fifth Detection—The plasma lysis processing makes nucleic acids, proteins, and other biomarkers available for extraction into fluid. The extractable biomaterials such as the nucleic acids, proteins, and other biomarkers may be characterized using polymerase chain reaction (PCR), antigen assay, and other biosensor techniques.

The present invention comprises a method of sorting and analyzing particles in an aerosol. The method generally comprises collecting an ambient aerosol; removing a portion of the fluid from the sample so as to produce a concentrated aerosol; exposing the concentrated aerosol to a laser, wherein the laser collides with the particles and scatters and/or absorbs; measuring the scattering/absorption of the laser; spraying the selected particles with an electrospray fluid; separating the electrosprayed particles from the non-electrosprayed particles; and collecting the electrosprayed particles and analyzing the electrosprayed particles.

The method will be described in further detail below, but it is noted that descriptions of some features of the method that overlap with the apparatus described above may not be repeated.

In the first step of the method, a sample of ambient aerosol is collected. By collected it is meant any means in which a sample of the ambient aerosol may be drawn into the apparatus to be subjected to the subsequent steps of the method independently of the ambient aerosol.

In the second step of the method, the collected aerosol is concentrated by removing a portion of the fluid from the aerosol, preferably without also removing any of the particles contained in the aerosol. By reducing the amount of fluid in the aerosol, the aerosol becomes more concentrated with particles and subsequent treatment of the particles is easier to perform. In a preferred embodiment, more than about 50% of the fluid in the ambient aerosol sample is removed and more preferably more than about 90% of the fluid is removed.

The step of removing fluid from the aerosol sample may also be combined with removing large particles from the aerosol sample. The targeted particles for subsequent treatment in the method are normally of a small size, and therefore the first step towards separating and collecting selected small particles may be achieved by removing both excess fluid and particles that are larger than a certain size. Specialized design of a virtual impactor aerosol concentrator may achieve very sharp cut-off points for the particles based on their size and density.

After a concentrated aerosol has been produced, the next step in the method is to expose the concentrated aerosol to a laser. The laser light collides and/or absorbs with the particles in the aerosol, thus causing the laser light to scatter or absorb to varying degrees based upon the characteristics of the particle. These measurements are used to analyze and perform a first identification of the particle.

In a preferred embodiment, a single laser is split into two beams, and the pulsed or continuous laser beams scatter and/or absorb after colliding with the particles. By measuring the scattering and/or absorption, as well as the velocity, size and particle fluorescent signature of the particles, a first identification may be achieved. The particles may optionally be pretreated to enhance the scattering by adding amino acid binding material to enhance fluorescence.

The measurements of the first identification and corresponding data interpreted therefrom may be used in the step of electrospraying at least one particle of interest with at least one electrospray fluid. The electrospray fluid preferably coats the particle and adds a charge to the particle. The electrospray fluid may be any suitable material for adding a charge to a particle and also may include an immunoassay or nanoassay that attaches to the particle as discussed above.

The measurements taken from the first identification may be used to determine when and at which particles to spray the electrospray fluid. In a preferred embodiment, the velocity measurement of the particle of interest is used to time the firing of the electrospray nozzle by also knowing the distance between where the particle collides with the laser and where the electrospray fluid is fired. The particle diameter measurement may be used to determine at which particles to fire the electrospray fluid. For example, the method can be adjusted such that only particles with a predetermined size are coated with an electrospray fluid. In this manner, any particles not having the specified size are not electrosprayed, while the particles with the designated size are electrosprayed using the velocity measurement discussed previously. The fluorescent signature of the particles determined from the first identification may be used for identification purposes and may therefore be used to determine at which particles to fire an electrospray fluid. Additionally, it should be noted that, where multiple electrospray fluids may be fired, the size and fluorescent signature measurement may be used to determine which electrospray fluid to fire at the particle.

In order to assure that the electrospray fluid coats only the selected particle, the method of the present invention preferably requires that the electrospraying be initiated and terminated in less than about one millisecond. By requiring a short burst of electrospray fluid, the chance of coating a particle not intended to be coated is significantly decreased. Thus, the efficiency of the sorting is improved.

In the next step of the method, the electrosprayed particles are separated from the non-electrosprayed particles and collected. In a preferred embodiment, the separation of electrosprayed particles from non-electrosprayed particles is achieved due to the charge that has been added to the electrosprayed particles. In a preferred embodiment, a first charged particle analyzer is provided that will attract charged particles due to electrostatic forces, and thereby sort the electrosprayed particles from the non-electrosprayed particles. The electrosprayed particles are attracted towards and settle on a first charged particle analyzer, while the non-electrosprayed particles collect in a separate area.

In the next step of the method, the electrosprayed particles which have been separated from non-electrosprayed particles and which have been collected on a first charged particle analyzer undergo a second, redundant analysis. The aim of the second analysis is to confirm the identity of the particles of interest, and any suitable means for analyzing the particles may be used. In the case of a disguised particle, the present method comprises removing the disguise by plasma lysis of the coating of the disguised particles. The plasma lysis involves subjecting the disguised particles to an ionizing gas that breaches the coating of the disguised particle, thereby exposing the payload or interstitial contents which may be chromosomal nucleic acid and proteins in the case of biological particles.

Once these components of the payload have been exposed, the method as described above may be repeated. For example, optical analysis such as IR spectroscopy may be performed on the exposed particles, followed by electrospraying, sorting and a second redundant analysis on a charged particle analyzer. The IR spectrum obtained during optical analysis may be used to determine biomarkers unique to the particle, such as the carbohydrates in the BG spores discussed above. In addition, the payload may be further identified by extracting chromosomal nucleic acid exposed by the plasma lysis and performing polymerase chain reaction (PCR) replication.

The foregoing description of the invention has been presented describing certain operable and preferred embodiments. It is not intended that the invention should be so limited since variations and modifications thereof will be within the skill of those skilled in the art, all of which are within the spirit and scope of the invention.

What is claimed is:

1. A method of performing redundant analysis of particles in an aerosol comprising the steps of:
    (1) collecting an aerosol comprising particles and fluid;
    (2) removing a portion of the fluid from the aerosol so as to produce a concentrated aerosol;
    (3) exposing the particles in the concentrated aerosol to a first laser beam;
    (4) measuring the scattering and absorption of said first laser beam;
    (5) selecting a first particle of interest based on a first analysis of said measured scattering and absorption;
    (6) spraying said first particle of interest with a first electrospray fluid to produce an electrosprayed first particle of interest;
    (7) isolating said electrosprayed first particle of interest; and
    (8) performing a second analysis of said electrosprayed first particle of interest.

2. The method as claimed in claim 1, wherein said concentrated aerosol comprises virtually no particles larger than a predetermined size.

3. The method as claimed in claim 1, wherein said first analysis comprises the comparison of said measured scattering and absorption to a previously measured scattering and absorption of a previously known particle of interest.

4. The method as claimed in claim 1, wherein said spraying with said first electrospray fluid is initiated and terminated in less than about 1 millisecond.

5. The method as claimed in claim 1, wherein there is an electric charge on said electrosprayed first particle of interest.

6. The method as claimed in claim 1, wherein said second analysis comprises the performance of a biosensor technique on said first particle of interest, wherein said biosensor technique is selected from the group consisting of polymerase chain reaction (PCR), antigen assay, and combinations thereof.

7. The method as claimed in claim 1, wherein said exposing further comprises the exposure of said particles in said concentrated aerosol to a second laser beam, and said spraying further comprises a second electrospray fluid.

8. The method as claimed in claim 1, wherein said second analysis comprises performing a plasma lysis of said electrosprayed first particle of interest, thereby exposing a first payload of said electrosprayed first particle of interest.

9. The method as claimed in claim 8, further comprising the steps of:
    (9) exposing said first payload to a second laser beam;
    (10) measuring the scattering and absorption of said second laser beam;
    (11) selecting a second particle of interest based on a third analysis of said measured scattering and absorption of said second laser beam;

(12) spraying said second particle of interest with a second electrospray fluid to produce an electrosprayed second particle of interest;

(13) isolating said electrosprayed second particle of interest; and

(14) performing a fourth analysis of said electrosprayed second particle of interest.

10. The method as claimed in claim 9, wherein said fourth analysis comprises the performance of a biosensor technique on said electrosprayed second particle of interest, wherein said biosensor technique is selected from the group consisting of polymerase chain reaction (PCR), antigen assay, and combinations thereof.

* * * * *